US00PP34686P2

(12) United States Plant Patent
Wood

(10) Patent No.: US PP34,686 P2
(45) Date of Patent: Oct. 25, 2022

(54) ***THUJA* PLANT NAMED 'SMTOM1'**

(50) Latin Name: *Thuja occidentalis*
Varietal Denomination: SMTOM1

(71) Applicant: Spring Meadow Nursery, Inc, Grand Haven, MI (US)

(72) Inventor: Timothy D. Wood, Spring Lake, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/540,989

(22) Filed: Dec. 2, 2021

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

*Primary Examiner* — Anne Marie Grunberg
(74) *Attorney, Agent, or Firm* — Cassandra Bright

(57) ABSTRACT

A new and distinct variety of *Thuja* plant named 'SMTOM1' is disclosed, characterized by vibrant golden foliage on plants having a conical habit. Foliage is dense and feathery. Plants reach a moderate size at maturity. The new cultivar is a *Thuja*, suitable for ornamental garden purposes.

2 Drawing Sheets

Latin name of the genus and species: *Thuja occidentalis*.
Variety denomination: 'SMTOM1'.

BACKGROUND OF THE INVENTION

The new cultivar, hereinafter referred to as 'SMTOM1', was discovered as part of a breeding program at a commercial nursery in Grand Haven, Mich. The intention of the breeding program was to develop new *Thuja* varieties with novel plant habits and golden foliage for commercial ornamental purposes. This new discovery is the result of an open-pollination of the seed parent *Thuja occidentalis* 'Golden Globe' (unpatented) with unidentified pollen parents conducted during 2003.

The new variety was first identified as an interesting new plant during 2007 at the same commercial nursery in Grand Haven, Mich. After identifying the new variety as a potentially interesting selection, the inventor first organized propagation of 'SMTOM1' by softwood cuttings at the same commercial nursery during 2007. The inventor continued controlled testing and propagation, assessing stability of the unique characteristics of this variety. At least thirteen generations have been reproduced and have shown that the unique features of this cultivar are stable and reproduced true to type.

SUMMARY OF THE INVENTION

The cultivar 'SMTOM1' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SMTOM1' These characteristics in combination distinguish 'SMTOM1' as a new and distinct *Thuja* cultivar:

1. Narrow pyramidal mature plant habit.
2. Soft, feathery branchlets.

3. Vibrant golden foliage color, most pronounced on new growth.
5. Moderate size at maturity.

COMPARISON TO PARENT VARIETY

'SMTOM1' is similar in most horticultural characteristics to the parent variety *Thuja occidentalis* 'Golden Globe'. Plants of the new cultivar 'SMTOM1' however, differ in the following:

1. The new variety grows to 3 to 4 feet wide at reaching a height of 12 to 15 feet. The parent variety grows twice this wide (6 to 8 feet) at the same height.

COMMERCIAL COMPARISON

*Thuja* 'SMTOM1' can be compared to the commercial variety *Thuja* 'Yellow Ribbon', unpatented. Plants are similar in most horticultural characteristics, however, plants of the new variety differ in the following:

1. Plant shape of 'SMTOM1' is more flared at base than this comparator.
2. Foliage of 'SMTOM1' is more brightly yellow colored than this comparator.
3. Foliage of 'SMTOM1' is more dense than foliage of this comparator.

BRIEF DESCRIPTION OF THE PHOTOGRAPHS

Figure 1:
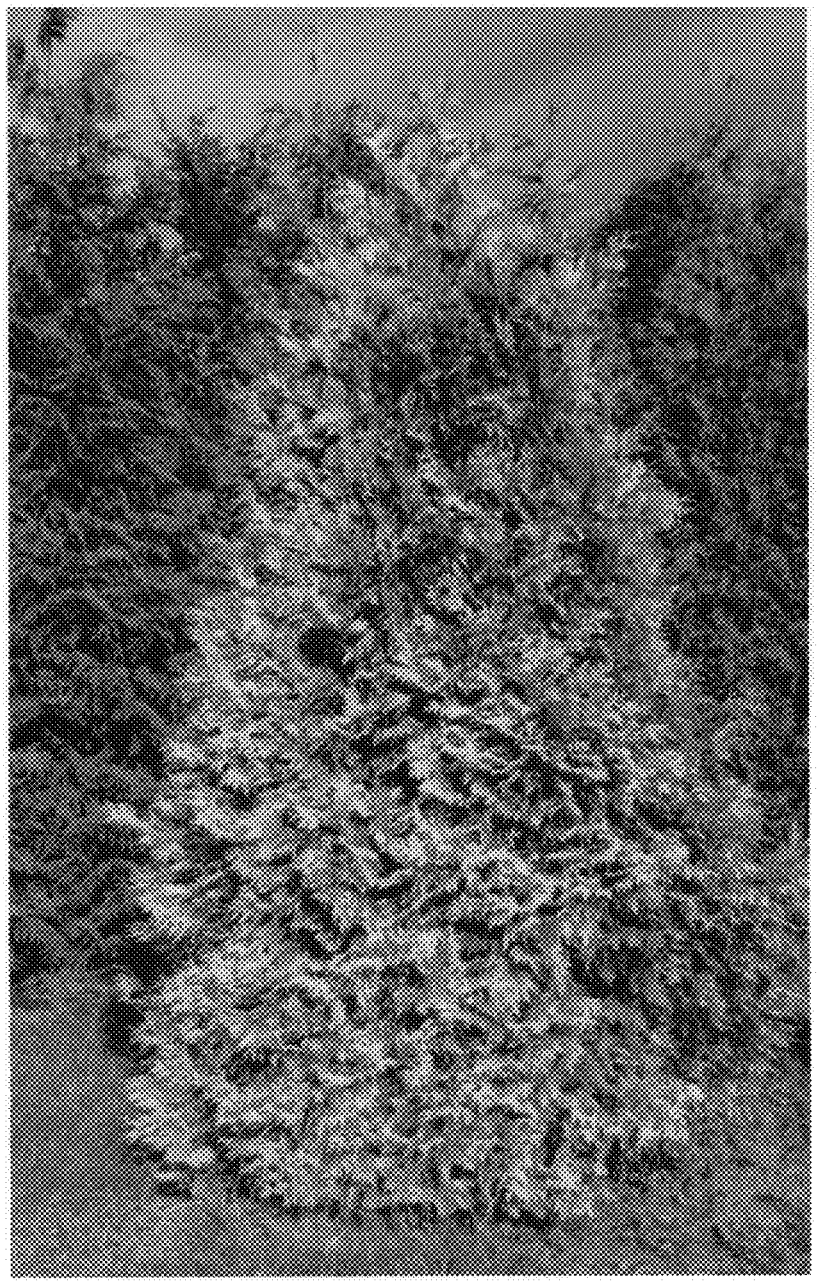

The accompanying photograph in FIG. 1 illustrates in full color a typical plant of 'SMTOM1' grown outdoors in Grand Haven, Mich. The plants are approximately 8 years old, in the ground.

Figure 2:
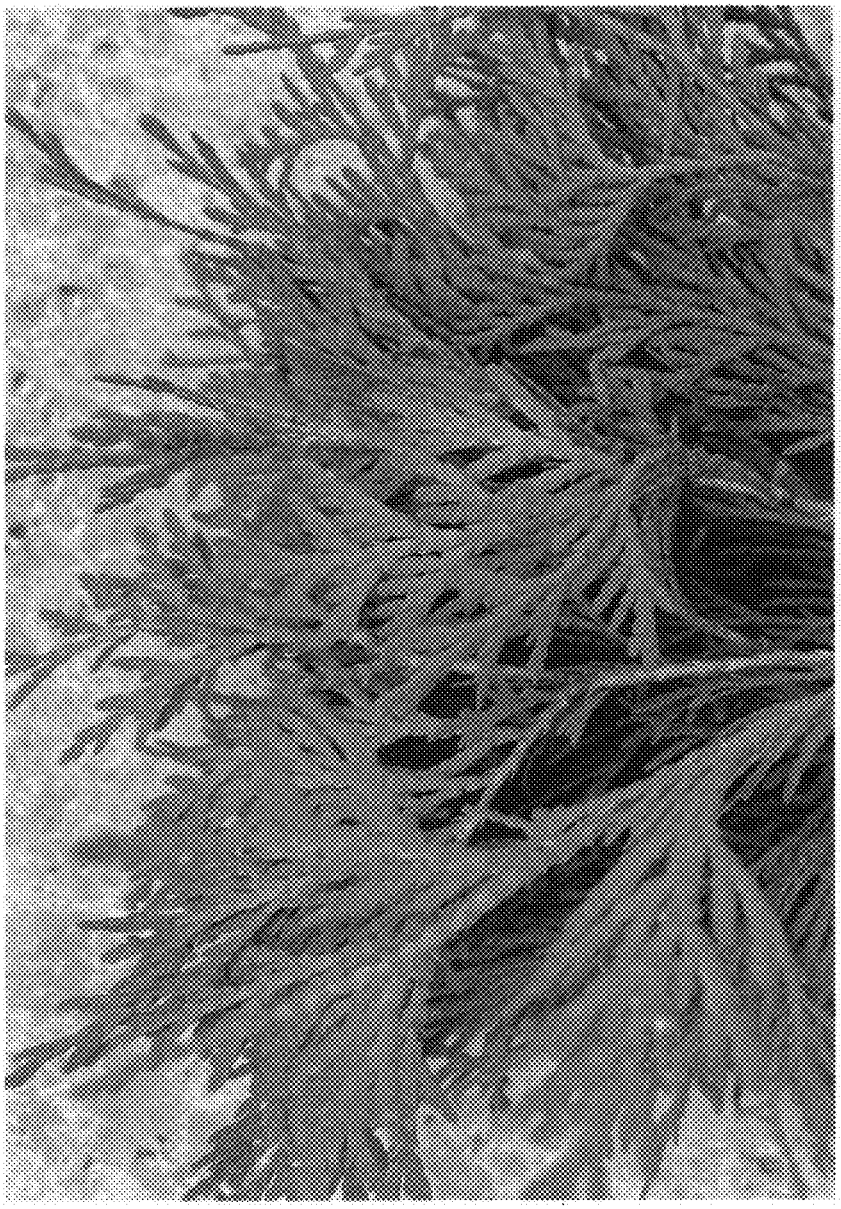

FIG. 2 illustrates a close up view of the foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SMTOM1' plants grown outdoors in Dayton, Oreg. Plants are approximately 1-2 years old, in a 1 gallon nursery container. Measurements and numerical values represent averages of typical plant types.

Botanical classification: *Thuja occidentalis* 'SMTOM1'.

PROPAGATION

Time to rooting: About 45 days at approximately 18-27° C.

Root description: Moderately dense branching. Slightly woody, both fine and thick roots present. Colored white and tan, not accurately measured with The R.H.S. chart.

PLANT

Growth habit: Perennial evergreen tree with a narrow pyramidal habit at maturity.

Height: 33 cm at approximately 1-2 years. 360 cm to 450 cm at maturity.

Plant spread: 17 cm. 90 cm to 120 cm at maturity.

Typical growth rate: Slow.

Pinching required: No.

Branching characteristics: Outwards at acute angles.

Average number of lateral branches: About 20 major lateral branches.

Length of lateral branches: 9 to 16 cm.

Diameter of lateral branches: 5 mm.

Lateral branch shape in cross section: Oval.

Lateral branch texture: Rough, scaly.

Branch angle: About 15 to 30 degrees from center.

Lateral branch color: Greyed-Orange N170B with mature bark near Grey-Brown 199B.

Lateral branch strength: Very strong, flexible.

Internode length: Average range 1.1 to 1.8 cm.

Main stem:

*Diameter.*—About 2.5 cm at 2 years.

*Length.*—About 28 cm at 2 years.

*Color.*—Near RHS Greyed-Orange 174B.

*Texture.*—Slightly scaly at 2 years.

FOLIAGE

Leaf:

*Arrangement.*—Alternate, overlapping scales.

*Quantity.*—About 8 to 10 per 1 cm of linear leaflet length.

*Shape.*—Scales.

*Average length.*—1 mm.

*Average width.*—1 mm.

*Apex.*—Acuminate.

*Base.*—Truncate.

*Margin.*—Entire.

*Texture of top surface.*—Smooth, waxy.

*Texture of bottom surface.*—Smooth, waxy.

*Color.*—Young foliage upper side: Yellow-green 150B. Young foliage under side: Yellow-green 154B. Mature foliage upper side: Green 143C. Mature foliage under side: Green 143C. Winter coloration: No noticeable change from mature foliage color.

*Venation.*—Indistinguishable from leaf blade.

*Leaf gland.*—Oblong, approximately 0.08 mm long and 0.05 mm long. Only visible under magnification. Colored near Yellow-Green 145B.

*Fragrance.*—None.

FLOWER

Flowering not observed.

OTHER CHARACTERISTICS

Disease and pest resistance: Neither resistance nor susceptibility observed.

Drought tolerance: No tolerance for drought.

Temperature tolerance: USDA Zones 3 through 8.

What is claimed is:

1. A new and distinct cultivar of *Thuja* plant named 'SMTOM1' as herein illustrated and described.

* * * * *